US005527981A

United States Patent [19]
Valyocsik

[11] Patent Number: 5,527,981
[45] Date of Patent: Jun. 18, 1996

[54] SORPTION SEPARATION WITH MCM-58

[75] Inventor: Ernest W. Valyocsik, Yardley, Pa.

[73] Assignee: Mobil Oil Corporation, Fairfax, Va.

[21] Appl. No.: 431,160

[22] Filed: Apr. 28, 1995

Related U.S. Application Data

[63] Continuation-in-part of Ser. No. 205,437, Mar. 4, 1994, Pat. No. 5,437,855, which is a continuation-in-part of Ser. No. 137,705, Oct. 18, 1993, abandoned.

[51] Int. Cl.$^6$ .................................................... C07C 7/12
[52] U.S. Cl. ........................................... 585/820; 585/825
[58] Field of Search ...................................... 585/820, 825

[56] References Cited

U.S. PATENT DOCUMENTS

| | | | |
|---|---|---|---|
| 3,702,886 | 11/1972 | Argauer et al. | 423/328 |
| 3,709,979 | 1/1973 | Chu | 423/328 |
| 3,832,449 | 8/1974 | Rosinski et al. | 423/328 |
| 3,972,983 | 8/1976 | Ciric | 423/328 |
| 4,016,245 | 4/1977 | Plank et al. | 423/328 |
| 4,076,842 | 2/1978 | Plank et al. | 423/328 |
| 4,954,325 | 9/1990 | Rubin et al. | 423/328 |
| 4,981,663 | 1/1991 | Rubin | 423/277 |
| 5,437,855 | 8/1995 | Valyocsik | 502/62 |
| 5,441,721 | 8/1995 | Valyocsik | 502/62 |

*Primary Examiner*—Sharon Gibson
*Attorney, Agent, or Firm*—Dennis P. Santini

[57] ABSTRACT

This invention relates to use of synthetic porous crystalline material MCM-58 as a sorbent composition for separating at least one component from a mixture of components.

15 Claims, 3 Drawing Sheets

SORPTION SEPARATION WITH MCM-58

CROSS-REFERENCE TO RELATED APPLICATIONS

This is a continuation-in-part of application Ser. No. 08/205,437, filed Mar. 4, 1994, now U.S. Pat. No. 5,437,855 which is a continuation-in-part of application Ser. No. 08/137,705, filed Oct. 18, 1993 abandoned.

BACKGROUND OF THE INVENTION

1. Field of the Invention

This invention relates to use of MCM-58, a composition of synthetic porous crystalline material, as a sorbent composition component for separating at least one component from a mixture of components. The sorption separation process comprises contacting the mixture with a sorbent composition comprising MCM-58.

2. Description of the Prior Art

Porous inorganic solids have found utility as separations media for industrial application. The openness of their microstructure allows molecules access to the relatively large surface areas of these materials that enhance their sorption utility. The porous materials in use today can be sorted into three broad categories using the details of their microstructure as a basis for classification. These categories are the amorphous and paracrystalline supports, the crystalline molecular sieves and modified layered materials. The detailed differences in the microstructures of these materials manifest themselves as important differences in both catalytic and sorptive behavior of the materials, as well as in differences in various observable properties used to characterize them, such as their surface area, the sizes of pores and the variability in those sizes, the presence or absence of X-ray diffraction patterns and the details in such patterns, and the appearance of the materials when their microstructure is studied by transmission electron microscopy and electron diffraction methods.

Amorphous and paracrystalline materials represent an important class of porous inorganic solids that have been used for many years in industrial applications. Typical examples of these materials are the amorphous silicas commonly used in catalyst formulations and the paracrystalline transitional aluminas used as solid acid catalysts and petroleum reforming catalyst supports. The term "amorphous" is used here to indicate a material with no long range order and can be somewhat misleading, since almost all materials are ordered to some degree, at least on the local scale. An alternate term that has been used to describe these materials is "X-ray indifferent". The microstructure of the silicas consists of 100–250 Angstrom particles of dense amorphous silica (*Kirk-Othmer Encyclopedia of Chemical Technology*, 3rd. ed., vol. 20, 766–781 (1982)), with the porosity resulting from voids between the particles. Since there is no long range order in these materials, the pores tend to be distributed over a rather large range. This lack of order also manifests itself in the X-ray diffraction pattern, which is usually featureless.

Paracrystalline materials such as the transitional aluminas also have a wide distribution of pore sizes, but better defined X-ray diffraction patterns usually consisting of a few broad peaks. The microstructure of these materials consists of tiny crystalline regions of condensed alumina phases and the porosity of the materials results from irregular voids between these regions (K. Wefers and Chanakya Misra, "Oxides and Hydroxides of Aluminum" Technical Paper No. 19 Revised, Alcoa Research Laboratories, 54–59 (1987)). Since, in the case of either material, there is no long range order controlling the sizes of pores in the material, the variability in pore size is typically quite high. The sizes of pores in these materials fall into a regime called the mesoporous range, including, for example, pores within the range of about 15 to about 200 Angstroms.

In sharp contrast to these structurally ill-defined solids are materials whose pore size distribution is very narrow because it is controlled by the precisely repeating crystalline nature of the materials' microstructure. These materials are called "molecular sieves", the most important examples of which are zeolites.

Zeolites, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials are known as "molecular sieves" and are utilized in a variety of ways to take advantage of these properties.

Such molecular sieves, both natural and synthetic, include a wide variety of positive ion-containing crystalline silicates. These silicates can be described as a rigid three-dimensional framework of $SiO_4$ and Periodic Table Group IIIB element oxide, e.g., $AlO_4$, in which the tetrahedra are cross-linked by the sharing of oxygen atoms whereby the ratio of the total Group IIIB element, e.g., aluminum, and Group IVB element, e.g., silicon, atoms to oxygen atoms is 1:2. The electrovalence of the tetrahedra containing the Group IIIB element, e.g., aluminum, is balanced by the inclusion in the crystal of a cation, for example, an alkali metal or an alkaline earth metal cation. This can be expressed wherein the ratio of the Group IIIB element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No 3,702,886); zeolite ZSM-11 (U.S. Pat. No. 3,709,979); zeolite ZSM-12 (U.S. Pat. No. 3,832,449), zeolite ZSM-20 (U.S. Pat. No. 3,972,983); ZSM-35 (U.S. Pat. No. 4,016,245); zeolite ZSM-23 (U.S. Pat. No. 4,076,842); zeolite MCM-22 (U.S. Pat. No. 4,954,325); and zeolite MCM-35 (U.S. Pat. No. 4,981,663), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the SiO$_2$/Al$_2$O$_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicate of varying alumina and metal content.

Certain layered materials, which contain layers capable of being spaced apart with a swelling agent, may be pillared to provide materials having a large degree of porosity. Examples of such layered materials include clays. Such clays may be swollen with water, whereby the layers of the clay are spaced apart by water molecules. Other layered materials are not swellable with water, but may be swollen with certain organic swelling agents such as amines and quaternary ammonium compounds. Examples of such non-water swellable layered materials are described in U.S. Pat. No. 4,859,648 and include layered silicates, magadiite, kenyaite, trititanates and perovskites. Another example of a non-water swellable layered material, which can be swollen with certain organic swelling agents, is a vacancy-containing titanometallate material, as described in U.S. Pat. No. 4,831,006.

Once a layered material is swollen, the material may be pillared by interposing a thermally stable substance, such as silica, between the spaced apart layers. The aforementioned U.S. Pat. Nos 4,831,006 and 4,859,648 describe methods for pillaring the non-water swellable layered materials described therein and are incorporated herein by reference for definition of pillaring and pillared materials.

Other patents teaching pillaring of layered materials and the pillared products include U.S. Pat. Nos. 4,216,188; 4,248,739; 4,176,090; and 4,367,163; and European Patent Application 205,711.

The X-ray diffraction patterns of pillared layered materials can vary considerably, depending on the degree that swelling and pillaring disrupt the otherwise usually well-ordered layered microstructure. The regularity of the microstructure in some pillared layered materials is so badly disrupted that only one peak in the low angle region on the X-ray diffraction pattern is observed, at a d-spacing corresponding to the interlayer repeat in the pillared material. Less disrupted materials may show several peaks in this region that are generally orders of this fundamental repeat. X-ray reflections from the crystalline structure of the layers are also sometimes observed. The pore size distribution in these pillared layered materials is narrower than those in amorphous and paracrystalline materials but broader than that in crystalline framework materials.

It is an object of the present invention to provide a method for selectively separating components in a mixture with a new sorbent composition.

SUMMARY OF THE INVENTION

The present invention is directed to use of a novel porous crystalline composition of matter, named MCM-58, as a sorbent composition component for sorption separation of at least one component from a mixture of components. The calcined form of the porous crystalline material for use in this invention possesses a high sorption capacity. Also, MCM-58 is reproducibly synthesized in high purity, making it useful for this process.

An embodiment of the present process provides for sorption of at least one component from a mixture of components having different sorption characteristics with respect to the structure of MCM-58. The mixture is contacted with a catalytically inactive form of sorbent composition comprising MCM-58 to selectively sorb at least one component of the mixture.

Another embodiment of the present process provides for sorption and retention of hydrocarbons contained in exhaust gases. This process embodiment involves contacting the gas with the sorbent at low temperature, such as during the startup period of an internal combustion engine, and removing the hydrocarbons from the exhaust gas prior to releasing same to the atmosphere.

DESCRIPTION OF SPECIFIC EMBODIMENTS

Figure 1:
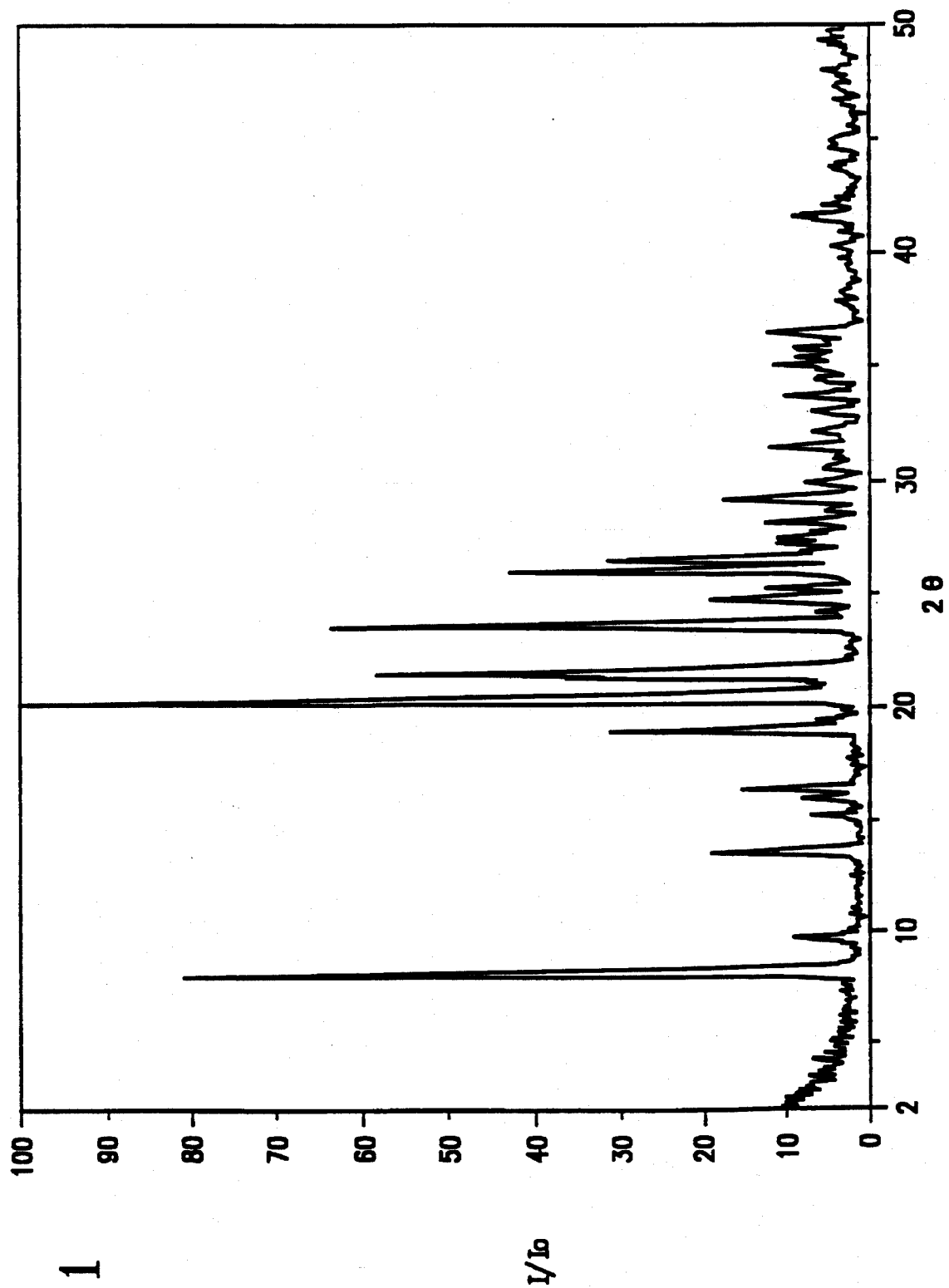
FIG. 1 shows the X-ray diffraction pattern of the assynthesized product of Example 6, hereinafter presented.

U.S. applications Ser. Nos. 08/205,437 and 08/137,705 are entirely incorporated herein by reference for definition of MCM-58 and its properties.

The crystalline MCM-58 material for use herein has a composition involving the molar relationship:

$$X_2O_3:(n)YO_2,$$

wherein X is a trivalent element, such as aluminum, boron, iron, indium, and/or gallium, preferably aluminum; Y is a tetravalent element such as silicon, tin, and/or germanium, preferably silicon; and n is from greater than about 10 to about 1000, usually from greater than about 10 to about 400, more usually from about 20 to about 200. In the assynthesized form, the material has a formula, on an anhydrous basis and in terms of moles of oxides per n moles of YO$_2$, as follows:

$$(0.1-2)M_2O:(0.2-2)R:X_2O_3:nYO_2$$

wherein M is an alkali or alkaline earth metal, and R is an organic moiety. The M and R components are associated with the material as a result of their presence during crystallization, and are easily removed by post-crystallization methods hereinafter more particularly described.

The MCM-58 for use in the invention is thermally stable and in the calcined form exhibits significant hydrocarbon sorption capacity. To the extent desired, the original sodium and/or potassium cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Metal ions for this purpose include rare earth metals and metals of Groups IIA, IIIA, IVA, IB, IIB, IIIB, IVB and VIII of the Periodic Table of the Elements.

In the as-synthesized form, the crystalline MCM-58 material for use in the invention appears to be a single crystalline phase. It can be prepared in essentially pure form with little or no detectable impurity crystal phases and has an X-ray diffraction pattern which is distinguished from the patterns of other known as-synthesized or thermally treated crystalline materials by the lines listed in Table I below:

TABLE I

| Interplanar d-Spacing (A) | Relative Intensity, I/Io × 100 |
|---|---|
| 10.89 ± 0.30 | s-vs |
| 9.19 ± 0.30 | vw |
| 6.55 ± 0.29 | vw-w |
| 5.86 ± 0.28 | vw-w |
| 5.57 ± 0.27 | vw-w |
| 5.43 ± 0.26 | vw-w |
| 4.68 ± 0.25 | vw-m |
| 4.36 ± 0.25 | w-vs |
| 4.17 ± 0.23 | vw-m |
| 4.12 ± 0.23 | vw-s |
| 3.78 ± 0.20 | wv-s |
| 3.61 ± 0.15 | vw-w |
| 3.54 ± 0.15 | vw |
| 3.44 ± 0.15 | vw-m |
| 3.37 ± 0.15 | vw-m |
| 3.06 ± 0.15 | vw-w |
| 2.84 ± 0.15 | vw |
| 2.72 ± 0.13 | vw |
| 2.66 ± 0.12 | vw |
| 2.46 ± 0.12 | vw |
| 2.17 ± 0.10 | vw |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (80–100), s=strong (60–80), m=medium (40–60), w=weak (20–40), and vw=very weak (0–20). It should be understood that diffraction data listed for this sample as single lines may diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history.

When used as a sorbent component, MCM-58 may be subjected to treatment to remove part or all of any organic constituent. The crystalline material can also be used as a sorbent in intimate combination with components such as tungsten, vanadium, molybdenum, rhenium, nickel, cobalt, chromium, manganese, or a noble metal such as platinum or palladium. Such components can be in the composition by way of cocrystallization, exchanged into the composition to the extent a Group IIIA element, e.g., aluminum, is in the structure, impregnated therein or intimately physically admixed therewith. Such components can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The metal containing MCM-58 may have essentially no acid activity, or it may have substantial acid activity to provide for dual functional catalysis. The catalytic activity of MCM-58 can be adjusted from essentially zero to high activity, depending on the particular use thereof.

The crystalline MCM-58 material can be transformed by thermal treatment. This thermal treatment is generally performed by heating at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C.

MCM-58 can be prepared from a reaction mixture containing sources of alkali or alkaline earth metal (M), e.g., sodium and/or potassium, cation, an oxide of trivalent element X, e.g., aluminum and/or boron, an oxide of tetravalent element Y, e.g., silicon, directing agent (R), and water, said reaction mixture having a composition, in terms of mole ratios of oxides, within the following ranges:

| Reactants | Useful | Preferred |
|---|---|---|
| $YO_2/X_2O_3$ | 15 to 1000 | 25 to 500 |
| $H_2O/YO_2$ | 5 to 200 | 20 to 100 |
| $OH^-/YO_2$ | 0 to 3 | 0.10 to 0.50 |
| $M/YO_2$ | 0 to 3 | 0.10 to 2 |
| $R/YO_2$ | 0.02 to 1.0 | 0.10 to 0.50 |

In this synthesis method, the preferred source of $YO_2$ comprises predominately solid $YO_2$, for example at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) is preferred for MCM-58 formation from the above mixture. Preferably, therefore, the $YO_2$, e.g., silica, source contains at least about 30 wt. % solid $YO_2$, e.g., silica, and more preferably at least about 40 wt. % solid $YO_2$, e.g., silica.

The organic directing agent R for use herein above is either the cation benzylquinuclidinium, having a formula $C_{14}H_{20}N^+$, or the cation benzyltropanium, having a formula $C_{15}H_{22}N^+$, and may be represented as follows:

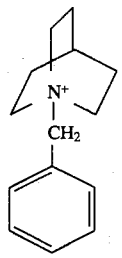

or

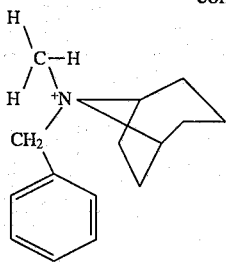

The sources of these organic cations may be, for example, the halide, e.g., chloride or bromide, or hydroxide salt. The source of organic directing agents used in the following examples was synthesized as follows:

(1) Benzylquinuclidinium halide, i.e., bromide, was synthesized by reacting benzylbromide and quinuclidine in absolute ethanol solvent in a flask equipped with a reflux condenser, a thermometer and a stirrer. The flask was charged with 60.0 grams of benzylbromide with 200 ml of absolute ethanol. Then 33.4 grams of quinuclidine dissolved in 300 ml of absolute ethanol was transferred to the flask. Heating and stirring of the flask reaction mixture commenced immediately.

The reaction mixture was refluxed ($\approx$70° C.) overnight with stirring before quenching the reaction vessel in a dry ice-acetone bath to −40° C. The cold crystalline product was separated from the solvent, filtered, and washed with anhydrous diethylether on a Büchner funnel. The crystals were dried in an air stream, then chemically analyzed. The benzylquinuclidium bromide product of this example was found to be composed of 56.13 wt. % C, 7.46 wt. % H, 4.66 wt. % N and 28.13 wt. % Br;

(2) Benzyltropanium halide, i.e., bromide, was synthesized by reacting benzylbromide and tropane in absolute ethanol solvent in a flask equipped with a reflux condenser, a thermometer and a stirrer. The flask was charged with 60.0 grams of benzylbromide with 300 ml of absolute ethanol. Then 37.6 grams of tropane dissolved in 300 ml of absolute ethanol was transferred to the flask. Heating and stirring of the flask reaction mixture commenced immediately.

The reaction mixture was refluxed ($\approx$70° C.) overnight with stirring before quenching the reaction vessel in a dry ice-acetone bath to −40° C. The cold crystalline product was separated from the solvent, filtered, and washed with anhydrous diethylether on a Büchner funnel. The benzyltropanium bromide product crystals were then dried in an air stream.

Crystallization of the MCM-58 can be carried out at either static or stirred conditions in a suitable reactor vessel, such as for example, polypropylene jars or teflon lined or stainless steel autoclaves. The total useful range of temperatures for crystallization is from about 80° C. to about 250° C. for a time sufficient for crystallization to occur at the temperature used, e.g., from about 12 hours to about 100 days. Thereafter, the crystals are separated from the liquid and recovered.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

Synthesis of MCM-58 may be facilitated by the presence of at least 0.01 percent, preferably 0.10 percent and still more preferably 1 percent, seed crystals (based on total weight) of crystalline product.

The MCM-58 crystals can be shaped into a wide variety of particle sizes for use herein. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where MCM-58 is molded, such as by extrusion, the crystals can be extruded before drying or partially dried and then extruded.

The MCM-58 or sorbent composition comprising MCM-58 for use in the present invention should usually be dehydrated, at least partially. This can be done by heating to a temperature in the range of 200° C. to 595° C. in an inert atmosphere, such as air, nitrogen, etc. and at atmospheric, subatmospheric or superatomospheric pressures for between 30 minutes and 48 hours. Dehydration can also be performed at room temperature merely by placing the molecular sieve in a vacuum, but a longer time is required to obtain a sufficient amount of dehydration.

The present sorbent composition has sorption affinity for hydrocarbons and utility for removing atmospheric pollutants from industrial exhaust gases.

The term industrial exhaust gas as used herein means any waste gas which is formed in an industrial process or operation and which is normally disposed of by discharge to the atmosphere. The composition of such a gas varies and depends on the particular process or operation which leads to its formation. When formed in the combustion of fossil fuels, it will generally contain oxygen, nitrogen, steam, carbon dioxide, carbon monoxide, unburned hydrocarbons, especially olefins and aromatics resulting from incomplete combustion, and $NO_x$ at relatively low levels, such as up to about 1,000 ppm of nitric oxide plus nitrogen dioxide. Sulfur-containing fuels will produce an exhaust gas that contains some $SO_x$ including sulfur dioxide and sulfur trioxide.

Industrial exhaust gases include flue gases produced, for example, by incinerators, turbines, $HNO_3$ plants, coalfired and fossil-fueled power plants, and internal combustion engines. Methods for removal of the pollutants include catalytic oxidation, e.g., of unburned hydrocarbons and carbon monoxide, reduction of $NO_x$ and adsorption or absorption of hydrocarbons and $SO_x$.

Examples of particular applications of the sorbent for use herein include removal of unburned hydrocarbons such as $C_3$–$C_6$ paraffins and olefins, and aromatics, from cold engine flue gas using the hydrogen or alkali metal ion exchanged structure, which may be impregnated with oxidation metal components including, for example, Pt, Cu, Ni and V.

MCM-58 can also be used as an adsorbent and separation vehicle in fine chemical applications. At least one component in a mixture of components can be partially or substantially separated from a mixture of components having different sorption characteristics with respect to the MCM-58 by contacting the mixture with the MCM-58 to selectively sorb the one component. Examples of this include contacting a mixture comprising water and at least one hydrocarbon component, whereby at least one hydrocarbon component is selectively sorbed. Another example includes sorption of at least one hydrocarbon component from a mixture comprising same and at least one additional hydrocarbon component.

For some uses, it is desired to incorporate the MCM-58 crystal with another material resistant to high temperatures and other harsh conditions. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. These materials may be incorporated into naturally occurring clays, e.g., bentonite and kaolin, to improve the crush strength of the sorbent under commercial operating conditions. Said materials, i.e., clays, oxides, etc., function as binders for the MCM-58. It is desirable to provide a sorbent composition having good crush strength because in commercial use it is desirable to prevent the sorbent composition from breaking down into powder-like materials. These clay and/or oxide binders have been employed normally only for the purpose of improving the crush strength of the sorbent.

Naturally occurring clays which can be composited with MCM-58 include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with MCM-58 also include inorganic oxides, such as silica, zirconia, titania, magnesia, beryllia, alumina, and mixtures thereof.

In addition to the foregoing materials, MCM-58 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented. In the examples, whenever sorption data are set forth for comparison of sorptive capacities for 2,2-dimethylbutane (2,2-DMB) and n-hexane, they were Equilibrium Adsorption values determined as follows.

A weighed sample of the calcined adsorbent was contacted with the desired pure adsorbate vapor in an adsorption chamber, evacuated to less than 1 mm and contacted with 40 Torr of n-hexane or 2,2-DMB vapor, pressures less than the vapor-liquid equilibrium pressure of the respective adsorbate at 30° C. for n-hexane and 90° C. for 2,2-DMB. The pressure was kept constant (within about ±0.5 mm) by addition of adsorbate vapor controlled by a manostat during the adsorption period, which did not exceed about 8 hours. As adsorbate was adsorbed by the new crystal, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in mg/g of calcined adsorbent.

When Alpha Value is examined, it is noted that the Alpha Value is an approximate indication of the acid catalytic activity of a crystalline material compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$). The Alpha Test is described in U.S. Pat. No. 3,354,078; in the *Journal of Catalysis*, 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis*, 61, 395.

EXAMPLES 1–11

Experiments were conducted for synthesis of crystalline product material. In these experiments, $Al_2(SO_4)_3 \cdot 18H_2O$ and KOH pellets were dissolved in deionized water. The benzylquinuclidinium bromide prepared as above was then dissolved in the solution. Colloidal silica sol (30 wt. % $SiO_2$) was then mixed into the solution. The mixture was stirred for 2 minutes to produce a uniform, fluid hydrogel, having, respectively, the compositions shown in Table II where R is the cation of benzylquinuclidinium bromide.

The hydrogel of each experiment was then transferred to a 300 ml stainless steel autoclave equipped with a stirrer. The autoclave was capped and sealed; and 400 psig of inert gas was introduced into the autoclave. Stirring and heating were started immediately. Crystallizations were carried out at 170° C. with stirring.

Crystalline products were recovered, filtered, washed with deionized water, and dried on a filter funnel in an air stream under an infrared lamp. The dried crystalline powder products were then submitted for X-ray diffraction and chemical analysis.

TABLE II

| | Mixture Composition (mole ratios) * | | | |
|---|---|---|---|---|
| Example | $SiO_2$/ $Al_2O_3$ | $K^+$/ $SiO_2$ | Reaction time, days | Products |
| 1 | 10 | 1.10 | 7 | Zeolite other than MCM-58 |
| 2 | 25 | 0.62 | 7 | MCM-58 + mordenite |
| 3 | 30 | 0.57 | 7 | MCM-58 |
| 4 | 30 | 0.57 | 2 | MCM-58 |
| 5 | 30 | 0.57 | 7 | MCM-58 |
| 6 | 30 | 0.57 | 7 | MCM-58 |
| 7 | 30 | 0.57 | 3 | MCM-58 |
| 8 | 60 | 0.43 | 7 | MCM-58 |
| 9 | 60 | 0.43 | 7 | MCM-58 |
| 10 | 70 | 0.41 | 7 | MCM-58 |
| 11 | 180 | 0.34 | 7 | MCM-58 + α-quartz |

* $H_2O/SiO_2 = 40$, $OH^-/SiO_2 = 0.30$, $R/SiO_2 = 0.20$

The X-ray diffraction data for the as-synthesized products of Examples 6 and 7 are presented in Tables III and IV, respectively. The X-ray diffraction pattern generated by the product of Example 6 is presented in FIG. 1.

TABLE III

| Interplanar d-Spacing (Å) | I/I$_o$ |
|---|---|
| 10.87 | 95 |
| 9.18 | 7 |
| 6.55 | 14 |
| 5.86 | 6 |
| 5.57 | 5 |
| 5.43 | 12 |
| 5.02 | 1 |
| 4.68 | 26 |

TABLE III-continued

| Interplanar d-Spacing (A) | I/I$_o$ |
| --- | --- |
| 4.59 | 5 |
| 4.35 | 100 |
| 4.23 | <1 |
| 4.17 | 31 |
| 4.12 | 54 |
| 3.94* | <1* |
| 3.77 | 40 |
| 3.69 | 1 |
| 3.61 | 11 |
| 3.54 | 6 |
| 3.43 | 39 |
| 3.37 | 27 |
| 3.32* | 5* |
| 3.28 | 6 |
| 3.25 | 7 |
| 3.22 | 2 |
| 3.18 | 8 |
| 3.12 | 2 |
| 3.06 | 11 |
| 2.99 | 3 |
| 2.930 | 2 |
| 2.886 | 1 |
| 2.844 | 6 |
| 2.814 | <1 |
| 2.788 | 3 |
| 2.715 | 3 |
| 2.660 | 5 |
| 2.605 | 3 |
| 2.561 | 5 |
| 2.537 | 3 |
| 2.511 | 4 |
| 2.464 | 6 |
| 2.173 | 4 |

*Peak attributed to unidentified impurity phase

TABLE IV

| Interplanar d-Spacing (A) | I/I$_o$ |
| --- | --- |
| 10.91 | 73 |
| 9.21 | 6 |
| 6.57 | 16 |
| 5.87 | 5 |
| 5.58 | 5 |
| 5.43 | 12 |
| 5.03 | 2 |
| 4.97* | <1* |
| 4.69 | 27 |
| 4.59 | 4 |
| 4.36 | 100 |
| 4.23 | 7 |
| 4.17 | 28 |
| 4.13 | 58 |
| 3.95* | 1* |
| 3.77 | 64 |
| 3.70 | 1 |
| 3.61 | 17 |
| 3.55 | 10 |
| 3.44 | 42 |
| 3.37 | 26 |
| 3.33 | 7 |
| 3.30 | 5 |
| 3.29 | 8 |
| 3.26 | 8 |
| 3.22 | 6 |
| 3.18 | 9 |
| 3.12 | 2 |
| 3.07 | 16 |
| 3.00 | 7 |
| 2.934 | 3 |
| 2.889 | 4 |
| 2.845 | 10 |
| 2.816 | 4 |
| 2.790 | 5 |
| 2.716 | 5 |
| 2.661 | 8 |
| 2.607 | 5 |
| 2.561 | 7 |
| 2.536 | 4 |
| 2.513 | 7 |
| 2.464 | 11 |
| 2.173 | 4 |

*Peak attributed to unidentified impurity phase

Chemical analysis results for the as-synthesized products of Examples 2, 3, 5, 6, 8, 9, and 10 are presented in Table V.

TABLE V

| | Moles per Mole | | | | Composition[1] | | |
| --- | --- | --- | --- | --- | --- | --- | --- |
| | Moles C/ | | Al$_2$O$_3$ | | Al/ | K+/ | R[2]/ |
| Example | Mole N | N$_2$O: | K$_2$O: | SiO$_2$ | 100 Td | 100 Td | 100 Td |
| 2 | 17.1 | 0.45 | 0.71 | 20 | 9.0 | 6.4 | 4.1 |
| 3 | 13.0 | 0.83 | 0.18 | 25 | 7.4 | 1.3 | 6.1 |
| 5 | 17.5 | 0.55 | 0.99 | 26 | 7.1 | 7.1 | 3.9 |
| 6 | 17.1 | 0.58 | 0.93 | 24 | 7.7 | 7.1 | 4.5 |
| 8 | 17.0 | 0.64 | 1.36 | 32 | 5.9 | 8.1 | 3.9 |
| 9 | 15.7 | 1.32 | 0.21 | 46 | 4.2 | 0.88 | 5.5 |
| 10 | 17.4 | 1.58 | 0.45 | 66 | 2.9 | 1.3 | 4.6 |

[1]Calculated on the basis of 100(SiO$_2$ + AlO$_2$) tetrahedra
[2]R = benzylquinuclidinium cation There appears to be no clear trend in the alkali metal content per 100 tetrahedra, but there does appear to be approximately 4–6 template cations per 100 tetrahedra in the MCM-58 framework, indicating templating activity for the benzylquinuclidinium cation.

EXAMPLES 12–14

MCM-58 products of Examples 4, 5, and 6 were weighed into quartz boats, then placed into a Heviduty® tube furnace and sealed with nitrogen gas flowing through the furnace tube. The heating of the furnace was begun at 2° C./minute from room temperature to 538° C. When the furnace reached the maximum temperature, the flowing gas was switched to air, and the calcination of the zeolite was continued for 15 hours before termination.

The air calcined samples were ammonium exchanged with 1M NH$_4$NO$_3$ at 80° C. for 6 hours. After ammonium exchange, the zeolites were filtered, washed with deionized water, and dried in an air stream on the filter funnel under an infrared heat lamp.

The calcination procedure was repeated on the ammonium-exchanged materials in the tube furnace in the same manner as described above, except this time the samples were held at 538° C. for 8 hours to convert them to HMCM-58. Examples 12, 13, and 14 products were MCM-58 materials from the products of Examples 4, 5, and 6, respectively.

EXAMPLE 15

Samples of the HMCM-58 products of Examples 12, 13, and 14 were tested for acid catalytic activity in the Alpha Test and found to have Alpha Values of 521, 164, and 510, respectively.

Constraint Index

A convenient measure of the extent to which a crystalline material provides control to molecules of varying sizes to its internal structure is the Constraint Index (CI) of the material. Zeolites which provide a highly restricted access to and egress from their internal structures have a high value for the Constraint Index, and zeolites of this kind usually have pores of small size, e.g., less than 5 Angstroms. On the other hand, zeolites which provide relatively free access to their internal structures have a low value for the Constraint Index and usually have pores of large size, e.g., greater than 8 Angstroms. The method by which Constraint Index is determined is described fully in U.S. Pat. No. 4,016,218, incorporated herein by reference for details of the method.

Constraint Index values for some typical zeolites are as follows:

|  | CI (at test temperature) |
| --- | --- |
| ZSM-4 | 0.5 (316° C.) |
| ZSM-5 | 6–8.3 (371° C.–316° C.) |
| ZSM-11 | 5–8.7 (371° C.–316° C. |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 0.6–1.5 (399° C.–454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

EXAMPLE 16

The Constraint Index of the HMCM-58 product of Example 13 was determined to be 0.3 at 316° C. This value falls within the classification of the more open structures having 12-membered rings. Hence, it is concluded from the catalytic Constraint Index Test result that HMCM-58 contains at least a 12-membered ring structure.

EXAMPLE 17

Figure 2:
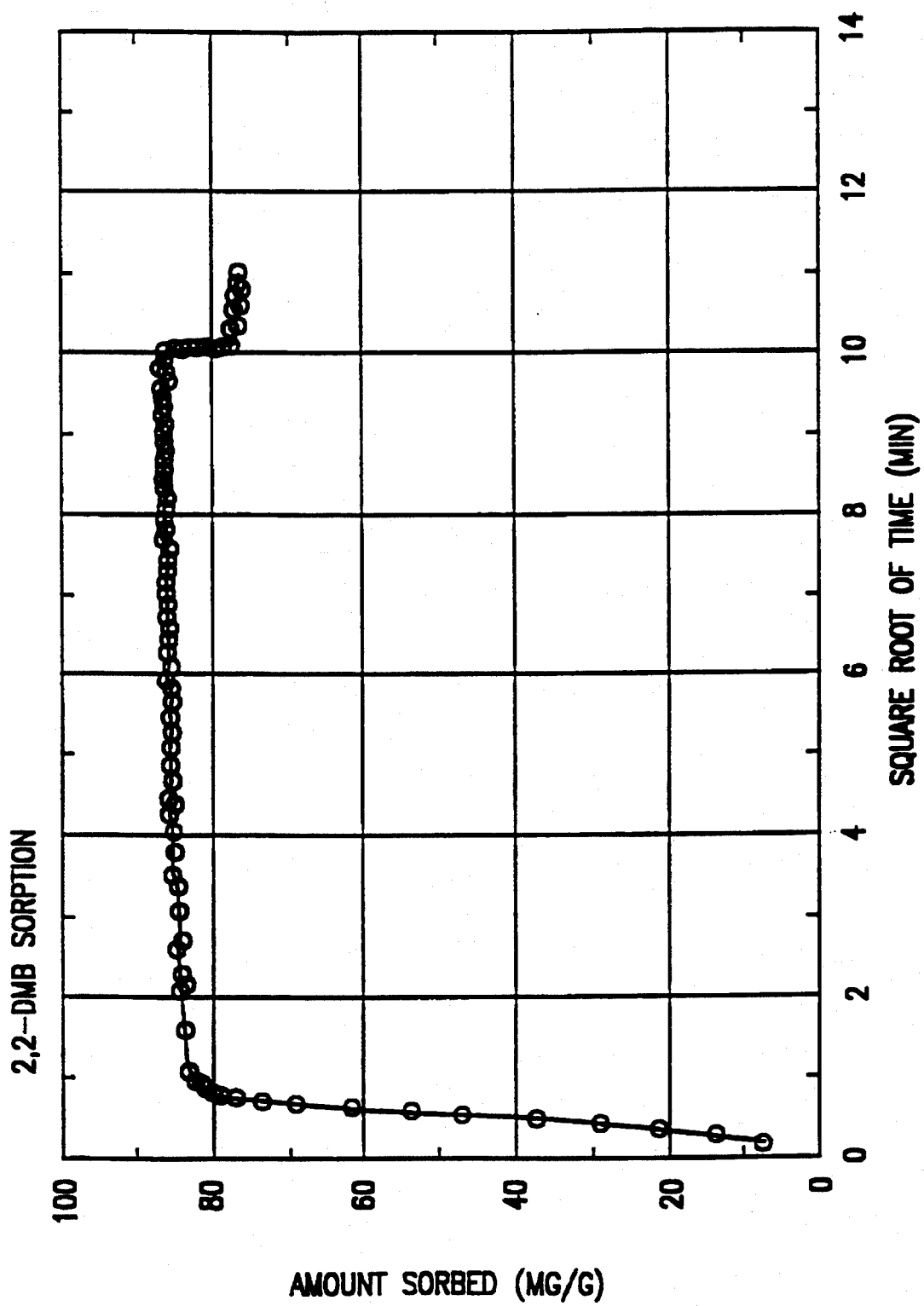
FIG. 2 shows the 2,2-dimethylbutane sorption isotherm for the product of Example 14, hereinafter presented.

A sample of the HMCM-58 product of Example 14 was subjected to sorption evaluation. FIG. 2 shows the 2,2-dimethylbutane (2,2-DMB) sorption measurements at 90° C. for this sample. The rapid uptake of 2,2-dimethylbutane indicates a very open pore structure.

EXAMPLE 18

Figure 3:
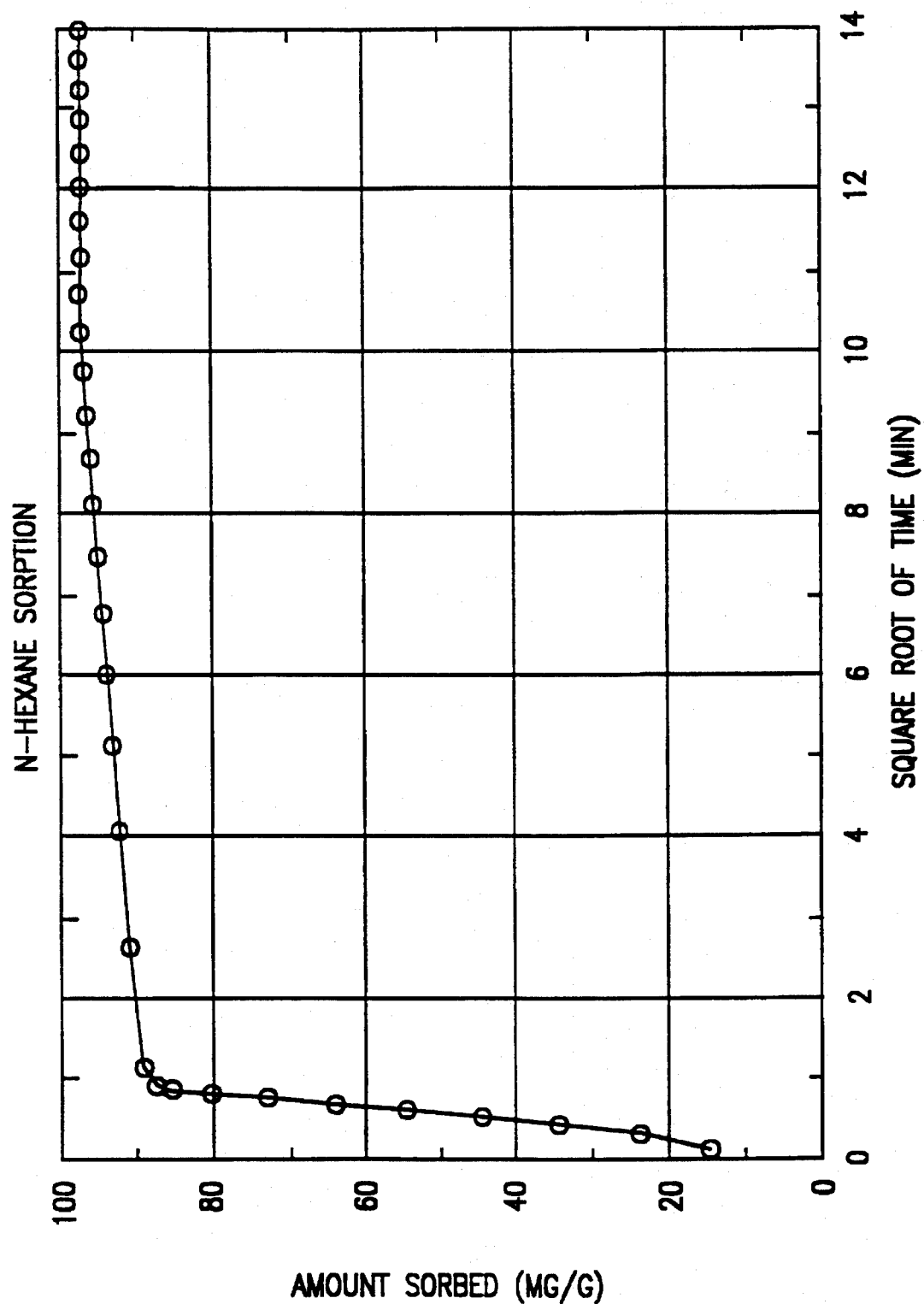
FIG. 3 shows the n-hexane sorption isotherm for the product of Example 14, hereinafter presented.

A sample of the HMCM-58 product of Example 14 was also subjected to n-hexane sorption evaluation. FIG. 3 shows the n-hexane sorption measurement at 30° C. for this sample. The rapid uptake of n-hexane into the HMCM-58 sample indicates a very open structure.

EXAMPLE 19

A solution was prepared by dissolving 0.99 g of boric acid and 4.93 g KOH pellets into 138.24 g deionized water. After the boric acid and KOH dissolved, 13.54 g of the organic template benzylquinuclidinium bromide was added to the solution and stirred until it dissolved. This solution was then transferred to a 300 ml stainless-steel autoclave. Now 48.0 g of colloidal silica sol (30% $SiO_2$) was added directly to the autoclave and the mixture was stirred for 2 minutes to produce a uniform, fluid hydrogel.

The autoclave was sealed, and stirring and heating were begun immediately. The autoclave was heated at a rate of 2° C./min. to the reaction temperature of 170° C. The autoclave was then held at 170° C. for 7 days with stirring at 400 rpm.

The resultant product was filtered, washed with boiling water, then dried in an air stream on the filter under an infrared heat lamp. The dried product was analyzed by X-ray powder diffraction analysis which showed that the material was crystalline borosilicate MCM-58.

EXAMPLES 20–25

In these experiments, $Al_2(SO_4)_3 \cdot 18H_2O$ and KOH pellets for potassium or NaOH pellets for sodium were dissolved in deionized water. Benzyltropanium bromide prepared as above was then dissolved in the solution. Colloidal silica sol (30 wt. % $SiO_2$) was then mixed into the solution. The mixture was stirred for 2 minutes to produce a uniform, fluid hydrogel, having, respectively, the compositions shown in Table VI where R is the cation of benzyltropanium bromide.

The hydrogel of each experiment was then transferred to a 300 ml stainless steel autoclave equipped with a stirrer. The autoclave was capped and sealed; and 400 psig of inert gas was introduced into the autoclave. Stirring and heating were started immediately. Crystallizations were carried out at 170° C. with stirring.

Crystalline products were recovered, filtered, washed with deionized water, and dried on a filter funnel in an air stream under an infrared lamp. The dried crystalline powder products were then submitted for X-ray diffraction and chemical analysis.

TABLE VI

| | Mixture Composition (mole ratios)[1] | | | | |
| --- | --- | --- | --- | --- | --- |
| Example | $SiO_2/$ $Al_2O_3$ | $K^+/$ $SiO_2$ | $Na^+/$ $SiO_2$ | Reaction time, days | Products |
| 20 | 15 | — | 0.44 | 7 | Mordenite |
| 21 | 25 | 0.62 | — | 7 | MCM-58 |
| 22 | 30 | — | 0.37 | 7 | Mordenite |
| 23 | 30 | 0.57 | — | 7 | MCM-58 |
| 24 | 30 | 0.57 | — | 7 | MCM-58 |
| 25 | 30 | 0.57 | — | 7 | MCM-58 |

[1]$H_2O/SiO_2$ = 40, $OH^-/SiO_2$ = 0.30, $R/SiO_2$ = 0.20

Chemical analysis results for the as-synthesized product of Example 23 is presented in Table VII.

TABLE VII

| | | Moles per Mole | | | Composition[1] | | |
|---|---|---|---|---|---|---|---|
| | Moles C/ | | Al$_2$O$_3$ | | Al/ | K+/ | R[2]/ |
| Example | Mole N | N$_2$O | K$_2$O | SiO$_2$ | 100 Td | 100 Td | 100 Td |
| 23 | 15.6 | 0.93 | 1.5 | 26.3 | 7.1 | 10 | 6.5 |

[1]Calculated on the basis of 100(SiO$_2$ + AlO$_2$) tetrahedra
[2]R = benzyltropanium cation Since there are approximately 6 template cations per 100 tetrahedra in the zeolite framework of the product of Example 23 templating activity for the benzyltropanium cation is indicated.

EXAMPLES 26–28

Zeolite products of Examples 23, 24, and 25 were weighed into quartz boats, then placed into a Heviduty® tube furnace and sealed with nitrogen gas flowing through the furnace tube. The heating of the furnace was begun at 2° C./minute from room temperature to 538° C. When the furnace reached the maximum temperature, the flowing gas was switched to air, and the calcination of the zeolite was continued for 15 hours before termination.

The air calcined samples were ammonium exchanged with 1M NH$_4$NO$_3$ at 80° C. for 6 hours. After ammonium exchange, the zeolites were filtered, washed with deionized water, and dried in an air stream on the filter funnel under an infrared heat lamp.

The calcination procedure was repeated on the ammonium-exchanged materials in the tube furnace in the same manner as described above, except this time the samples were held at 538° C. for 8 hours to convert them to the hydrogen form of the zeolite. Examples 26, 27, and 28 products were zeolite materials from the products of Examples 23, 24, and 25, respectively.

EXAMPLE 29

A quantity of the MCM-58 product of Example 5, having a Constraint Index of 0.3 at 316° C. is calcined in air at 540° C. for four hours and cooled to room temperature in dry helium. The treated MCM-58 is inserted into a quartz reactor tube having an inside diameter of 1 inch. The MCM-58 is calcined in air at 540° C. for four hours and cooled to 90° C. in nitrogen. A gas stream containing 1,500 ppm propylene in nitrogen is blown through the bed of MCM-58 at 400 cc/minute for 30 minutes. The effluent gas stream is collected and analyzed for hydrocarbon content, which proves to contain less than the inlet concentration due to adsorption and retention of propylene by the MCM-58 sorbent.

EXAMPLE 30

The sorbent bed of Example 29 is calcined in air at 540° C. for four hours and cooled to room temperature in dry helium. It is then contacted for 10 minutes with 10 g of m-xylene which contains 1 wt % p-xylene as an impurity. After contact, the p-xylene impurity content of the liquid proves to be reduced due to selective adsorption of p-xylene by the MCM-58.

What is claimed is:

1. A process for separating at least one component from a mixture of components in the vapor or liquid phase having differential sorption characteristics with respect to a sorbent composition wherein said at least one component is selectively sorbed by said sorbent composition in preference to at least one other component of said mixture of components, said sorbent composition comprising a synthetic porous crystalline material characterized by an X-ray diffraction pattern including values substantially as set forth in Table I of the specification and having a composition comprising the molar relationship $$X_2O_3:(n)YO_2,$$

wherein n is from greater than about 10 to about 1000, X is a trivalent element, and Y is a tetravalent element.

2. The process of claim 1 wherein said crystalline material is characterized by an X-ray diffraction pattern including values substantially as set forth in Table III of the specification.

3. The process of claim 1 wherein said crystalline material is characterized by an X-ray diffraction pattern including values substantially as set forth in Table IV of the specification.

4. The process of claim 1 wherein n is from greater than about 10 to about 400.

5. The process of claim 1 wherein n is from about 20 to about 200.

6. The process of claim 1 wherein said crystalline material comprises cations selected from the group consisting of hydrogen, hydrogen precursors, rare earth metals, and metals of Groups IIA, IIIA, IVA, IB, IIB, IIIB, IVB, VIB and VIII of the Periodic Table of the Elements, and combinations thereof.

7. The process of claim 1 wherein X is a trivalent element selected from the group consisting of boron, iron, indium, gallium, aluminum, and a combination thereof; and Y is a tetravalent element selected from the group consisting of silicon, tin, germanium, and a combination thereof.

8. The process claim 1 wherein X comprises aluminum, boron, or a combination thereof, and Y comprises silicon.

9. The process of claim 1 wherein X comprises aluminum and Y comprises silicon.

10. The process of claim 6 wherein said cations comprise hydrogen or a hydrogen precursor.

11. The process of claim 6 wherein said cations comprise metals.

12. The process of claim 1 wherein said sorbent composition comprises a matrix selected from the group consisting of alumina, silica, zirconia, titania, magnesia, beryllia, and a combination thereof.

13. The process of claim 1 in which the mixture comprises water and at least one hydrocarbon component, at least one hydrocarbon component of the mixture being selectively sorbed on said sorbent in preference to the water in the mixture.

14. The process of claim 1 in which the mixture comprises at least two hydrocarbon components, at least one of which is selectively sorbed on said sorbent in preference to at least one other hydrocarbon component of the mixture.

15. The process of claim 1 in which the mixture comprises an alcohol and at least one hydrocarbon component, at least one hydrocarbon component of the mixture being selectively sorbed on said sorbent in preference to the alcohol in the mixture.

* * * * *